United States Patent [19]

Brennan

[11] Patent Number: 4,602,091

[45] Date of Patent: Jul. 22, 1986

[54] PRODUCTION OF ETHYLENEDIAMINE AND N-AMINOETHYLPIPERAZINE FROM PIPERAZINE

[75] Inventor: Michael E. Brennan, Austin, Tex.

[73] Assignee: Texaco Inc., White Plains, N.Y.

[21] Appl. No.: 573,773

[22] Filed: Jan. 25, 1984

[51] Int. Cl.$^4$ .......................................... C07D 241/04
[52] U.S. Cl. ................................................. 544/402
[58] Field of Search ......................................... 544/402

[56] References Cited

U.S. PATENT DOCUMENTS

| | | | |
|---|---|---|---|
| 3,037,023 | 5/1962 | Moss et al. | 260/268 |
| 3,037,025 | 5/1962 | Godfrey | 260/268 |
| 3,151,115 | 9/1964 | Moss et al. | 260/268 |
| 3,297,700 | 1/1967 | Muhlbauer et al. | 260/268 |
| 3,341,600 | 9/1967 | Cour et al. | 260/584 |
| 3,383,417 | 5/1968 | Lichtenwalter | 260/584 |
| 3,793,397 | 2/1974 | Lichtenwalter | 260/288 |

Primary Examiner—Donald G. Daus
Assistant Examiner—Cecilia Shen
Attorney, Agent, or Firm—Jack H. Park; Kenneth R. Priem

[57] ABSTRACT

Piperazine is substantially selectively converted to ethylenediamine and N-aminoethylpiperazine by catalytically reductively aminating piperazine in the presence of added hydrogen, ammonia and (optionally) water under reductive amination conditions selected to provide a piperazine conversion of not more than about 30%.

10 Claims, No Drawings

PRODUCTION OF ETHYLENEDIAMINE AND N-AMINOETHYLPIPERAZINE FROM PIPERAZINE

BACKGROUND OF THE INVENTION

1. Technical Field of the Invention

This invention relates to the conjoint production of ethylenediamine and N-aminoethylpiperazine from piperazine.

More particularly, this invention is directed to a process wherein piperazine is reacted with ammonia in the presence of hydrogen and a reductive amination catalyst and in the optional presence of water to provide a reaction product comprising a predominant amount of ethylenediamine and N-aminoethylpiperazine.

2. Description of the Prior Art

It is known, as illustrated for example by Moss et al. U.S. Pat. No. 3,037,023, to prepare heterocyclic compounds such as piperazine by the reductive amination of a feedstock such as monoethanolamine in the presence of hydrogen, ammonia and water and a reductive amination catalyst.

It is also known to prepare a plurality of compounds using the reductive reamination reaction. For example, Moss et al. U.S. Pat. No. 3,151,115 is directed to a two-step process for the manufacture of piperazine and N-aminoethylpiperazine; Muhlbauer at al. U.S. Pat. No. 3,297,700 is directed to a process for the preparation of piperazine and aminoethylpiperazine from monoethanolamine.

Cour et al. U.S. Pat. No. 3,341,600 is directed to the simultaneous production of N-aminoethylpiperazine, N-hydroxyethylpiperazine and aminoethylethanolamine from monoethanolamine.

BACKGROUND OF THE INVENTION

Piperazine is a material that is used commercially for the manufacture of a variety of products such as pharmaceuticals and anthelmintic drugs, etc. Piperazine can be manufactured, as illustrated by the prior art discussed above, by the reductive amination of monoethanolamine. Piperazine is also formed as a by-product during the manufacture of ethylenediamine from feedstocks such as ethylene dichloride, monoethanolamine, etc.

The reductive amination reaction is non-selective when aliphatic or heterocyclic amines are used as feedstocks in that a wide variety of reaction products are potentially obtainable and are frequently obtained. Moreover, these products tend to fall within a narrow boiling point temperature range making purification difficult. For example, when monoethanolamine is used as a feedstock for the preparation of piperazine by catalytic reductive amination, the following products are obtained:

TABLE 1

| REACTION PRODUCT COMPONENTS | |
|---|---|
| Compound | Boiling Pt., °C. |
| N—methylethylenediamine | 115 |
| Ethylenlediamine | 117 |
| N—ethylethylenediamine | 129 |
| 1-methylpiperazine | 135 |
| Piperazine | 145 |
| 1-ethylpiperazine | 156 |
| Diethylenetriamine | 207 |
| N—aminoethylpiperazine | 221 |

TABLE 1-continued

| REACTION PRODUCT COMPONENTS | |
|---|---|
| Compound | Boiling Pt., °C. |
| N—hydroxyethylpiperazine | 242 |
| 2-(2-aminoethylamino)-ethanol | 242 |

In view of the complexity and number of reactions and side reactions that take place during reductive amination of aliphatic amines, this process would not appear as a likely candidate for a method for producing ethylenedamine, an aliphatic diamine, from piperazine, a heterocyclic diamine.

Ethylenediamine is widely used in commerce for a variety of purposes including the preparation of pharmaceuticals, chelating agents, lubricating oil additives, insecticides, pesticides, corrosion inhibitors, epoxy curing agents, fabric softeners, paper chemicals, petroleum additives, ore flotation chemicals, synthetic waxes, etc. The commercial demand for ethylenediamine is significantly greater than the commercial demand for piperazine and has resulted in the construction of manufacturing facilities capable of generating millions of pounds per year of ethylenediamine.

One of the by-products that is formed during the manufacture of ethylenediamine is piperazine. Although piperazine is present as a by-product, the tonnage of ethylenediamine that is manufactured is such that the amount of piperazine available as a by-product may periodically exceed the market demand, for piperazine.

One of the derivatives of piperazine that is used commercially in significant quantities is N-aminoethylpiperazine, which is used as an epoxy curing agent, a catalyst for the manufacture of polyurethane forms, etc.

Heretofore, N-aminoethylpiperazine has been available only as a by-product from the manufacture of piperazine, as illustrated by the prior art mentioned above, or by direct synthesis from piperazine and monoethanolamine.

SUMMARY OF THE INVENTION

Piperazine has been characterized as a heterocyclic compound having a ring structure that is broken only with difficulty. Thus, for example, when monoethanolamine is reductively aminated over a hydrogenation/dehydrogenation catalyst (i.e., a reductive amination catalyst), the reaction mixture becomes progressively more complex as the severity of the reductive amination reaction is progressively increased and the average molecular weight of the reaction mixture progressively increases, characterized by a progressive increase in the formation of a tarry residue containing "polymerized" and/or "condensed" piperazino- and ethylenic piperazino-groups.

It has been surprisingly discovered, in accordance with the present invention, that piperazine can be substantially selectively converted to ethylenediamine and N-aminoethylpiperazine with only minor by-product and residue formation when piperazine is reacted with ammonia in the presence of a slight excess of hydrogen and (optionally) water in the presence of a reductive amination catalyst under controlled reductive amination conditions.

The reductive amination catalyst to be used in accordance with the present invention may be any one or more of the catalysts that have heretofore been proposed for this purpose. Thus, metals and/or oxides of copper, nickel, cobalt, platinum, palladium, rhodium, etc. may be used. Also, if desired, a promoting amount (e.g., 0.5 to 10 wt.%) of a normally nonreducable metal oxide may also be utilized, such as chromium oxide, molybdenum oxide, manganese oxide, thorium oxide, etc. The catalyst ma be prepared as a mixture of oxides, for example, nickel oxide-copper oxide-chromium oxide, etc. and then reduced to an active form wherein the copper and nickel exist in combination with the chromium oxide.

The catalyst may also be carried on an inert support, if desired, such as silica, alumina, etc.

Examples of suitable reductive animation catalysts are given, for example, in Moss U.S. Pat. No. 3,152,998.

Ammonia is used as a coreactant and is preferably used in excess. Thus, at least one and, more preferably, about 2 to 10 moles of amonia are used per mole of fresh piperazine feedstock.

Water may also be used as a feed component, particularly when it is desired to enhance the yield of N-aminoethylpiperazine. Normally, the water will comprise from about 5 to about 55 wt.% of the total normally liquid nonaqueous feed to the reactor.

The temperatures to be used in accordance with the present invention are suitably within the range of about 150° to about 250° C., and more preferably within the range of about 180° to about 230° C.

Total pressure to be used during the reaction may suitably be within the range of 1000 to about 5000 psig. and, more preferably, within the range of about 1000 to about 3000 psig.

It is important to use at least a slight excess of hydrogen in order to obtain N-aminoethylpiperazine and ethylenediamine. Thus, for example, from more than 100 to about 300 molar percent of hydrogen (e.g., 125 to 200 mol percent) may be used with good results. Additional amounts of hydrogen may be used, but there is no particular advantage in such use.

The conversion of piperazine to ethylenediamine and N-aminoethylpiperazine by the process of the present invention may be conducted continuously or on a batch basis. When the reaction is to be conducted batchwise, reaction conditions are selected such that the total conversion of piperazine amounts to not more than about 30%. Thus, using the paramaters mentioned above, on a batch basis, reaction time may suitably be within the range of about 1 to about 10 hours, such as from about 2 to about 6 hours. When the reaction is conducted on a continuous basis, the feed rate may suitably be within the range of about 0.1 to about 10 gm of feedstock per mililiter of catalyst per hour, and more preferably from about 0.25 to about 2 gm of feedstock per mililiter of catalyst per hour.

DESCRIPTION OF THE PREFERRED EMBODIMENTS

The present invention will be further illustrated by the following specific examples which are given by way of illustration and not as limitations on the scope of this invention. Where parts are mentioned, they are parts by weight unless otherwise affirmatively indicated. When pressures are given, they are pressures measured in pounds per square inch gauge, unless an alternative measure is affirmatively set forth.

EXAMPLE I

A clean and dry 1-l stirred stainless steel autoclave was charged with 172.3 g (2.0 moles) anhydrous piperazine and 25.0 g powdered ($\geq$40 mesh) proprietary nickel, copper, chromia catalyst or proprietary cobalt copper, chromia catalyst. The whole was purged well with hydrogen and then 204.4 g (12.0 moles) anhydrous liquid ammonia was added. The autoclave was then further pressured with hydrogen to 250 psig, heated to the desired temperature, repressured with hydrogen to 2500 psig and held 4.0 hours. The whole was repressured to 2500 psig with hydrogen during the run if necessary. After cooling to room temperature, the autoclave was vented and the contents recovered. Liquid effluent was separated from catalyst and analyzed by gas-liquid chromatography (GLC, A %, lights/H$_2$O free). The results are set forth in Table 2.

EXAMPLE II (Water and Solvent)

The procedure was identical to Example I except that 172.3 g deionized water was also added to the autoclave. The results are set forth in Table 3.

TABLE 2

| NB Page No. | Temp. °C. | Catalyst | % Piperazine Conv. | % Selectivity | | | | |
|---|---|---|---|---|---|---|---|---|
| | | | | EDA | NMP | NEP | AEP | Hvys≠ |
| 5339-33 | 198.6 | Ni—Cu—Cr | 4.6 | 32.6 | 4.3 | — | 63.0 | — |
| 5339-34 | 219.8 | " | 12.2 | 41.8 | 22.1 | — | 32.8 | — |
| 5339-76 | 200.5 | Co—Cu—Cr | 0.7 | — | — | — | 100.0 | — |
| 5339-77 | 223.0 | " | 8.4 | 33.3 | 4.8 | 2.4 | 34.5 | 16.7 |

≠Hvys. were shown to be considerably higher than indicated when reaction mixtures were examined on a second glc column.

TABLE 3

| NB Page No. | Temp. °C. | Catalyst | % Piperazine Conv. | % Selectivity | | | | |
|---|---|---|---|---|---|---|---|---|
| | | | | EDA | NMP | NEP | AEP | Hvys≠ |
| 5339-35 | 199.6 | Ni—Cu—Cr | 14.1 | 53.9 | 5.7 | 2.8 | 28.4 | — |
| 5339-36 | 223.2 | " | 35.5 | 18.0 | 19.4 | 13.8 | 31.5 | 4.2 |
| 5339-78 | 200.0 | Co—Cu—Cr | 3.7 | 43.2 | 2.7 | — | 40.5 | — |
| 5339-79 | 225.8 | " | 10.9 | 45.0 | 2.8 | 7.3 | 30.3 | 4.6 |

≠Hvys. were shown to be considerably higher than indicated when reaction mixtures were examined on a second glc column.

EXAMPLE III (Hydrogen Only)

Runs were as in Example I, except that 258.4 g (3.0 moles) piperazine was employed. Ammonia and solvent were deleted. The results are set forth in Table 4.

EXAMPLE IV

(Water Solvent)

Example III was repeated except that 400 g deionized water was also used. The results are set forth in Table 5.

TABLE 4

| NB Page No. | Temp. °C. | Catalyst | % Piperazine Conv. | % Selectivity | | | | |
|---|---|---|---|---|---|---|---|---|
| | | | | EDA | NMP | NEP | AEP | Hvys≠ |
| 5339-53 | 200.6 | Ni—Cu—Cr | 7.1 | — | 4.2 | 36.6 | 14.1 | 33.8 |
| 5339-54 | 224.6 | " | 76.2 | — | 10.6 | 40.8 | 8.1 | 25.5 |
| 5339-66 | 200.7 | Co—Cu—Cr | 12.7 | 1.6 | 3.9 | 37.8 | 28.3 | 21.2 |
| 5339-67 | 222.2 | " | 50.6 | — | 6.3 | 43.3 | 15.4 | 26.7 |

≠Hvys. were shown to be considerably higher than indicated when reaction mixtures were examined on a second glc column.

TABLE 5

| NB Page No. | Temp. °C. | Catalyst | % Piperazine Conv. | % Selectivity | | | | |
|---|---|---|---|---|---|---|---|---|
| | | | | EDA | NMP | NEP | AEP | Hvys≠ |
| 5339-57 | 200.2 | Ni—Cu—Cr | 12.5 | — | 1.6 | 40.8 | 32.8 | 16.8 |
| 5339-58 | 225.3 | " | 78.3 | 0.5 | 6.8 | 48.3 | 7.0 | 11.2 |
| 5339-68 | 198.2 | Co—Cu—Cr | 6.0 | — | 5.0 | 18.3 | 35.0 | 26.7 |
| 5339-69 | 224.0 | " | 20.0 | — | 5.0 | 26.0 | 25.5 | 30.5 |

≠Hvys. were shown to be considerably higher than indicated when reaction mixtures were examined on a second glc column.

As can be seen from the foregoing examples, piperazine is substantially selectively converted to ethylenediamine and aminoethylpiperazine when the reductive amination process is conducted in accordance with the present invention.

Example II illustrates that the yield of ethylenediamine relative to aminoethylpiperazine is enhanced when water is used as a coreactant and that there is a significant loss of yield when the overall conversion of the piperazine is more than about 30%.

Having thus described my invention, what is claimed is:

1. A method for the production of ethylenediamine and N-aminoethylpiperazine from piperazine which comprises contacting a feedstock consisting essentially of piperazine with a reductive amination catalyst under reductive amination conditions including a temperature within the range of about 150° to about 250° C. and a pressure of from about 0 to about 5000 psig in the presence of excess hydrogen and from about 1 to about 12 mols of ammonia per mole of piperazine, for a contact time for said reductive aminations conditions of temperature and pressure correlated to provide for a conversion of the piperazine of not more than about 30%, whereby a piperazine conversion product is obtained containing ethylenediamine and N-aminoethylpiperazine as the principle reaction products with only minor by-product and residue formation, said reductive amination catalyst consisting essentially of nickel or cobalt and copper and chromia.

2. A method as in claim 1 wherein the reductive amination catalyst is a nickel, copper, chromia catalyst.

3. A method as in claim 2 wherein from about 5 to about 55 wt.% of water is also used.

4. A method as in claim 1 wherein the reductive amination catalyst is a cobalt, copper, chromia catalyst.

5. A method as in claim 4 wherein from about 5 to about 55 wt.% of water is also used.

6. A method for the production of ethylenediamine and N-aminoethylpiperazine from piperazine which comprises the steps of contacting a feedstock consisting essentially of piperazine with a reductive amination catalyst under reductive amination conditions including a temperature within the range of about 180° to about 230° C., and a pressure within the range of about 1000 to about 3000 psig in the presence of excess hydrogen and from about 4 to about 8 mols of ammonia per mole of piperazine, for a contact time for said reductive amination conditions of temperature and pressure correlated to provide for a conversion of the piperazine of not more than about 30%, whereby a piperazine conversion product is obtained containing ethylenediamine and N-aminoethylpiperazine as the principle reaction products with only minor by-product and residue formation, said reductive amination catalyst consisting essentially of nickel or cobalt and copper and chromia.

7. A method as in claim 6 wherein the reductive amination catalyst is a nickel, copper, chromia catalyst.

8. A method as in claim 6 wherein the reductive amination catalyst is a nickel, copper, chromia catalyst and wherein from about 5 to about 55 wt.% of water is used.

9. A method as in claim 6 wherein the reductive amination catalyst is a cobalt, copper, chromia catalyst.

10. A method as in claim 6 wherein the reductive amination catalyst is a cobalt, copper, chromia catalyst and wherein from about 5 to about 55 wt.% of water is also used.

* * * * *